(12) United States Patent
Nowitzke et al.

(10) Patent No.: US 8,303,496 B2
(45) Date of Patent: Nov. 6, 2012

(54) INSTRUMENTS AND METHODS FOR SELECTIVE TISSUE RETRACTION THROUGH A RETRACTOR SLEEVE

(75) Inventors: Adrian M. Nowitzke, Wilston (AU); Eric S. Heinz, Mountain View, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 841 days.

(21) Appl. No.: 12/207,202

(22) Filed: Sep. 9, 2008

(65) Prior Publication Data

US 2009/0005646 A1 Jan. 1, 2009

Related U.S. Application Data

(62) Division of application No. 11/112,588, filed on Apr. 22, 2005, now Pat. No. 7,427,264.

(51) Int. Cl.
*A61B 1/32* (2006.01)

(52) U.S. Cl. ........................................ 600/210

(58) Field of Classification Search .................. 600/187, 600/190, 203, 205, 208, 210, 221, 215, 101, 600/114, 120, 123, 124, 153, 156, 184, 193
See application file for complete search history.

(56) References Cited

U.S. PATENT DOCUMENTS

| | | | | |
|---|---|---|---|---|
| 5,678,572 A | * | 10/1997 | Shaw et al. | 128/899 |
| 5,685,826 A | * | 11/1997 | Bonutti | 600/204 |
| 6,206,826 B1 | * | 3/2001 | Mathews et al. | 600/210 |
| 2005/0055032 A1 | * | 3/2005 | Lau et al. | 606/108 |
| 2007/0021656 A1 | * | 1/2007 | Martin et al. | 600/231 |

* cited by examiner

*Primary Examiner* — Cris L Rodriguez
*Assistant Examiner* — Eric Rosen

(57) ABSTRACT

Methods and instruments for performing surgery in a patient are provided that minimize tissue dissection and retraction to access locations within the patient. One specific application concerns devices, instruments and techniques that provide for selective retraction of tissue, neural elements, organs or other anatomical structures at locations distally of the retractor sleeve providing percutaneous access to the locations.

19 Claims, 8 Drawing Sheets

INSTRUMENTS AND METHODS FOR SELECTIVE TISSUE RETRACTION THROUGH A RETRACTOR SLEEVE

CROSS-REFERENCE TO RELATED APPLICATION

This application is a divisional of U.S. application Ser. No. 11/112,588, filed Apr. 22, 2005, now U.S. Pat. No. 7,427,264, the entire contents of which are hereby incorporated by reference.

BACKGROUND

Traditional surgical procedures for pathologies located deep within the body can cause significant trauma to the intervening tissues. These open procedures often require a long incision, extensive muscle stripping, prolonged retraction of tissues, denervation and devascularization of tissue. These surgeries can require operating room time of several hours and several weeks of post-operative recovery time due to the use of general anesthesia and the destruction of tissue during the surgical procedure. In some cases, these invasive procedures lead to permanent scarring and pain that can be more severe than the pain leading to the surgical intervention.

The development of percutaneous procedures has yielded a major improvement in reducing recovery time and post-operative pain because minimal muscle and tissue dissection is required and the procedures can be performed under local anesthesia. For example, minimally invasive surgical techniques are desirable for spinal and neurosurgical applications because of the need for access to locations deep within the body and the danger of damage to vital intervening tissues. While developments in minimally invasive surgery are steps in the right direction, there remains a need for further development in minimally invasive surgical devices and techniques that facilitate tissue retraction at locations within the body.

SUMMARY

Methods and instruments for performing surgery in a patient are provided that minimize tissue dissection and retraction to access locations within the patient distally beyond a distal end of a retractor sleeve. One specific application concerns devices, instruments and techniques that provide for selective retraction of tissue, neural elements, organs or other anatomical structures at locations distal of the distal end of the retractor sleeve providing a working channel for percutaneous access to the locations.

According to one aspect, there is provided an instrument for retracting tissue to access a location in a patient. The instrument includes an elongated retractor sleeve defining a channel extending therethrough between a proximal end and a distal end. A plurality of elongated retractor blades are mounted along the channel of the retractor sleeve. The retractor blades are selectively moveable relative to the retractor sleeve to extend the selected retractor blade distally from the distal end of the retractor sleeve and to withdraw an extended retractor blade proximally into the retractor sleeve.

According to another aspect, an instrument for retracting tissue to access a location in a patient includes an elongated retractor sleeve having an inner surface defining a channel extending therethrough between a proximal end and a distal end. A retaining member is positionable in the channel of the retractor sleeve. The retaining member includes a cylindrical body extending along the inner surface and forming a number of passages between the body and the inner surface. The body further defines a working channel extending between a distal end and a proximal end of the body. A number of retractor blades are mounted in respective ones of the passages. Each of the retractor blades are moveable distally and proximally from the respective passage relative to a distal end of the retractor sleeve.

According to a further aspect, a method for retracting tissue in a surgical procedure comprises: inserting a retractor sleeve into an incision of a patient; positioning a retaining member in a channel of the retractor sleeve, the retaining member defining a working channel extending at least partially along the channel of the retractor sleeve; inserting at least two retractor blades into passages between the retaining member and the retractor sleeve; advancing one of the at least two retractor blades distally from a distal end of the retractor sleeve; and positioning at least one surgical instrument through the retractor sleeve and retaining member.

These and other aspects will be discussed further below.

DESCRIPTION OF THE ILLUSTRATED EMBODIMENTS

Figure 1:
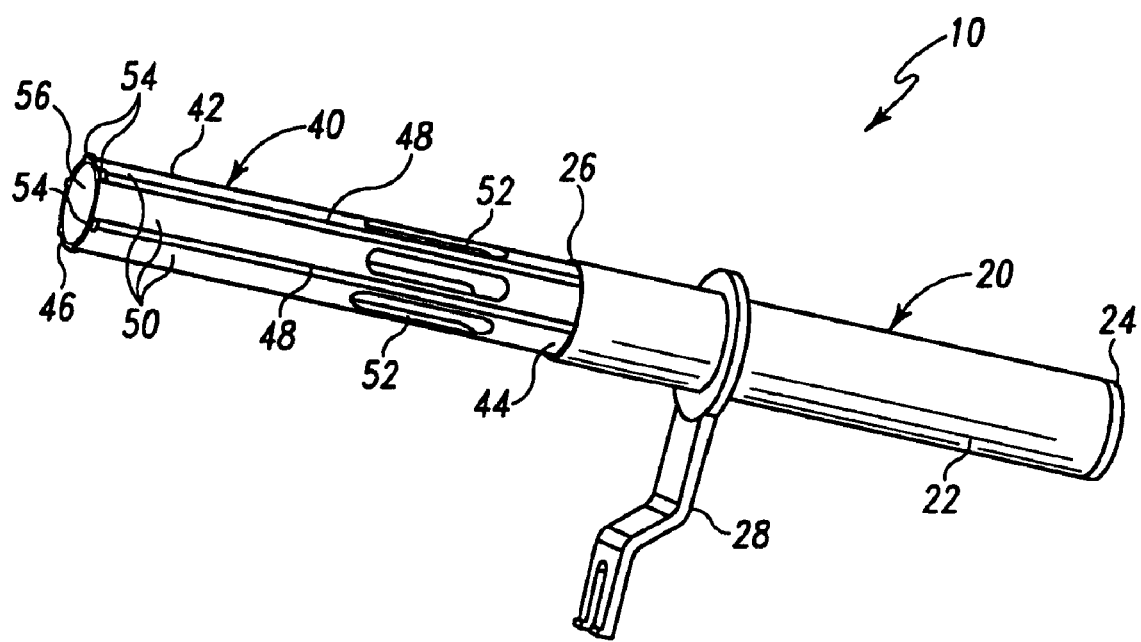
FIG. 1 is a perspective view of one embodiment retraction instrument with a retaining member positioned adjacent a proximal end of a retractor sleeve.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices and described methods, and such further applications of the principles of the invention as illustrated herein are contemplated as would normally occur to one skilled in the art to which the invention relates.

The instruments and methods discussed herein facilitate performance of surgeries at locations deep within a patient. A retractor sleeve is provided with the retraction instrumentation that is positionable through the skin and tissue of the patient with a proximal end opening accessible for placement of surgical instruments, implants and other devices through a working channel defined by the instrumentation. A plurality of retracting members are positioned about retractor sleeve adjacent the working channel, and one or more selected retracting members are movable distally from the retracting sleeve to provide selective tissue retraction at locations distal of the distal end of the retractor sleeve.

The instruments and methods have application in spinal surgery, including spinal surgeries that involve one or more techniques such as laminotomy, laminectomy, foramenotomy, facetectomy, discectomy, interbody fusion, spinal nucleus or disc replacement, and implant insertion, for example. The surgery can be performed through the working channel or passageway provided by the retraction instrumentation. Viewing of the surgical site at the working end of the retractor sleeve can be accomplished with optics mounted on the retractor sleeve, positioned over the retractor sleeve, and/or through a viewing system such as lateral fluoroscopy. The retractor sleeve can be positioned for any surgical approach to the spine, including anterior, posterior, posterior mid-line, lateral, postero-lateral, and/or antero-lateral approaches, and in other regions besides the spine.

Referring now to FIG. 1, there is shown a retraction instrument 10 including a retractor sleeve 20 and a retaining member 40. Retractor sleeve 20 includes an elongated body 22 extending between a distal end 24 and a proximal end 26. A retractor channel 30 extends between and opens at distal and proximal ends 24, 26. A mounting member 28 is engaged to and extends laterally from body 22 to facilitate coupling of retractor sleeve 20 with an arm engaged to a table, wall or other structure to facilitate maintaining the position of retraction instrument 10. Distal end 24 can be beveled to facilitate passage of retractor sleeve 20 through skin and tissue, although non-beveled ends are also contemplated.

Retaining member 40 includes an elongate body 42 extending between a distal end 44 and a proximal end 46. Elongate body 42 includes a cylindrical shape defining an elongate working channel 56 extending therethough between distal end 44 and proximal end 46. Body 42 extends continuously about working channel 56. Body 42 further includes a number of spaced, longitudinally extending and radially outwardly projecting flanges 48 extending between distal and proximal ends 44, 46. Wall portions 50 are included between adjacent ones of the flanges 48, and each of the wall portions 50 defines an elongated window 52 in communication with working channel 56. In the illustrated embodiment, windows 52 are offset longitudinally toward distal end 44 to facilitate retractor blade manipulation, although any location along body 42 is contemplated. Flanges 48 further each include an outwardly projecting retaining tab 54 at the proximal end thereof.

Figure 2:
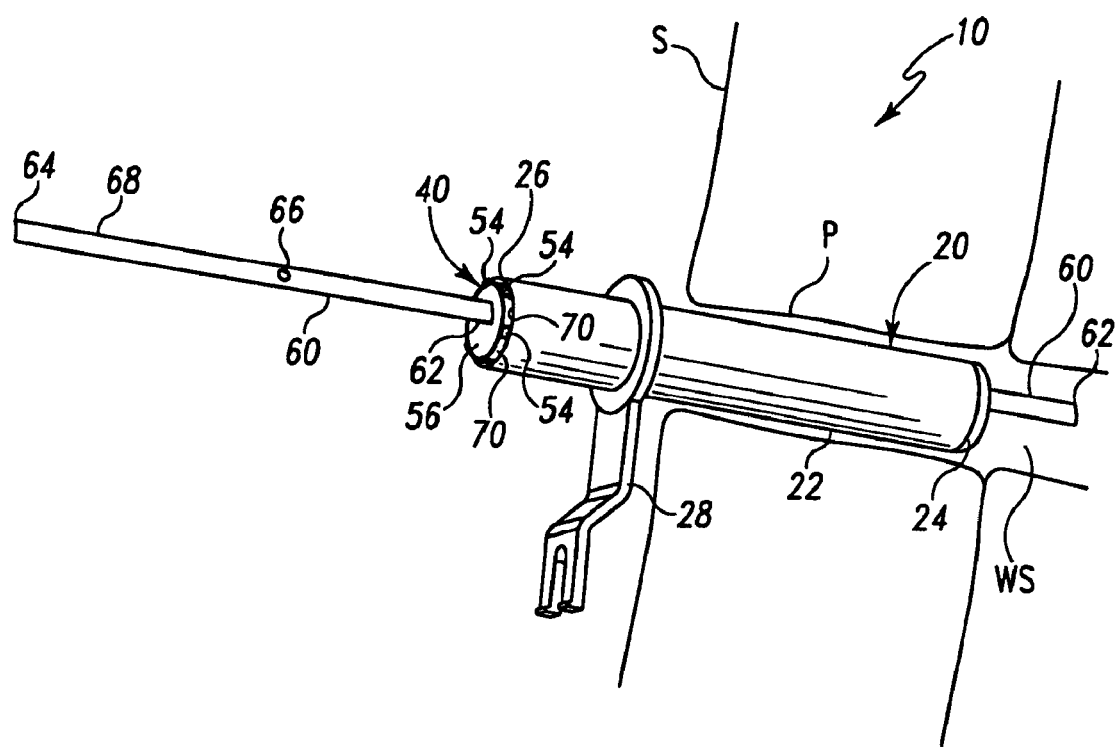
FIG. 2 is a perspective view of the instrument of FIG. 1 with the retaining member in the retractor sleeve and a retractor blade positioned for insertion between the retaining member and the retractor sleeve.

Referring now to FIG. 2, retaining member 40 is shown positioned in channel 30 of retractor sleeve 20. Tabs 54 engage proximal end 26 of retractor sleeve 20 to prevent over-insertion of retaining member 40 through the distal end opening of retractor sleeve 20, and to maintain distal end 44 at or adjacent distal end 24 of retractor sleeve 20. A passage 70 is formed between an inner wall surface of retractor sleeve 20 and each of the wall portions 50. The passages 70 also extend along the perimeter of retaining member 40 between adjacent ones of the longitudinal flanges 48. Working channel 56 extends along and is concentric with retractor channel 30.

Figure 3:
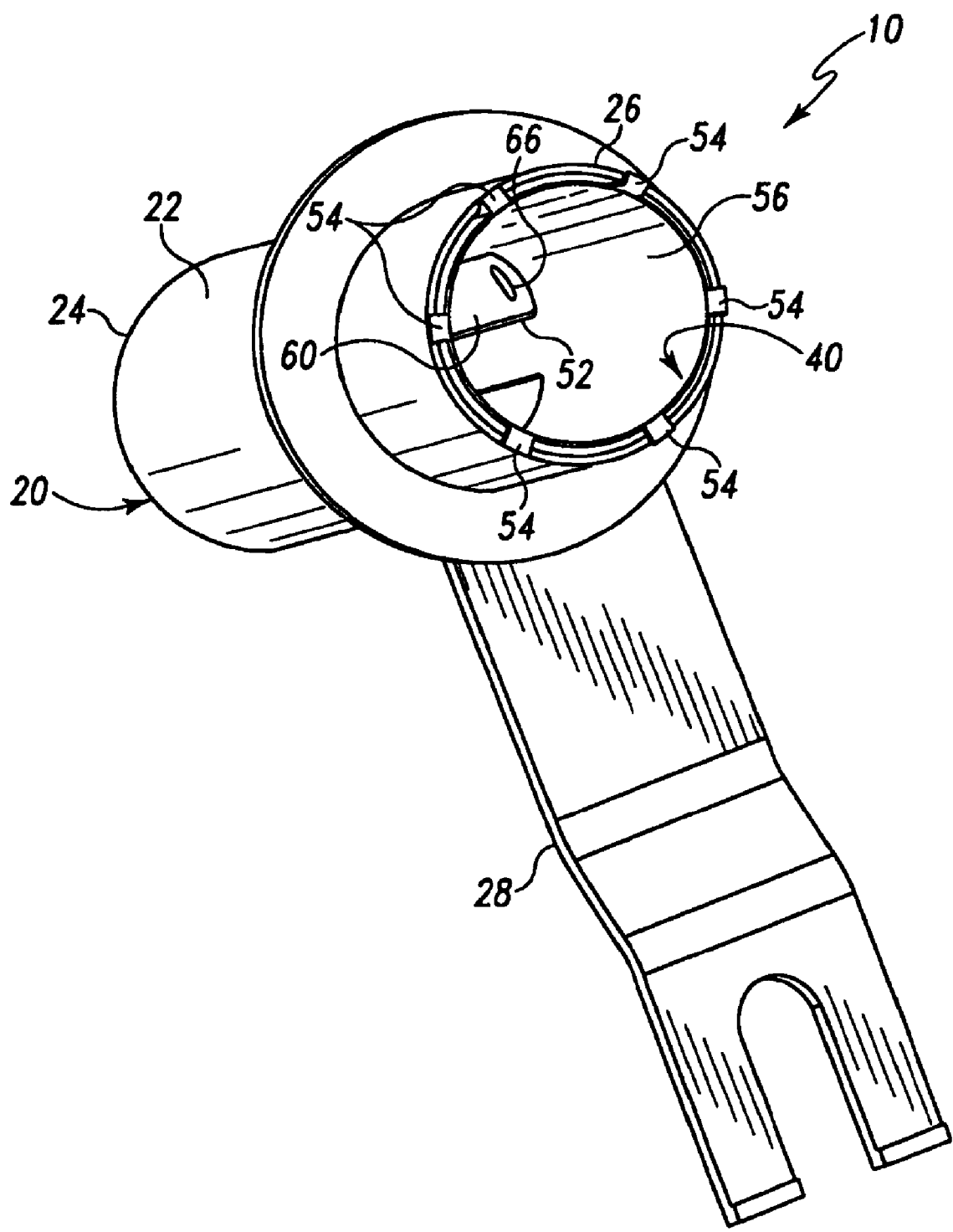
FIG. 3 is a perspective view looking toward the top of the retraction instrument of FIG. 1 with the retaining member and retractor blades positioned in the retractor sleeve.

A blade 60 is shown with an elongated, plate-like body 68 extending between a distal end 62 and a proximal end 64. A hole 66 is provided through body 68, the purpose for which will be discussed further below. Blade 60 is positionable into a respective one of the passages 70, and includes a length between distal and proximal ends 62, 64 so that blade 60 can be wholly contained between distal ends 24, 44 and proximal ends 26, 46 of the retractor sleeve 20 and retaining member 40. Furthermore, hole 66 is aligned with one of the windows 52, as shown in FIG. 3.

Figure 4:
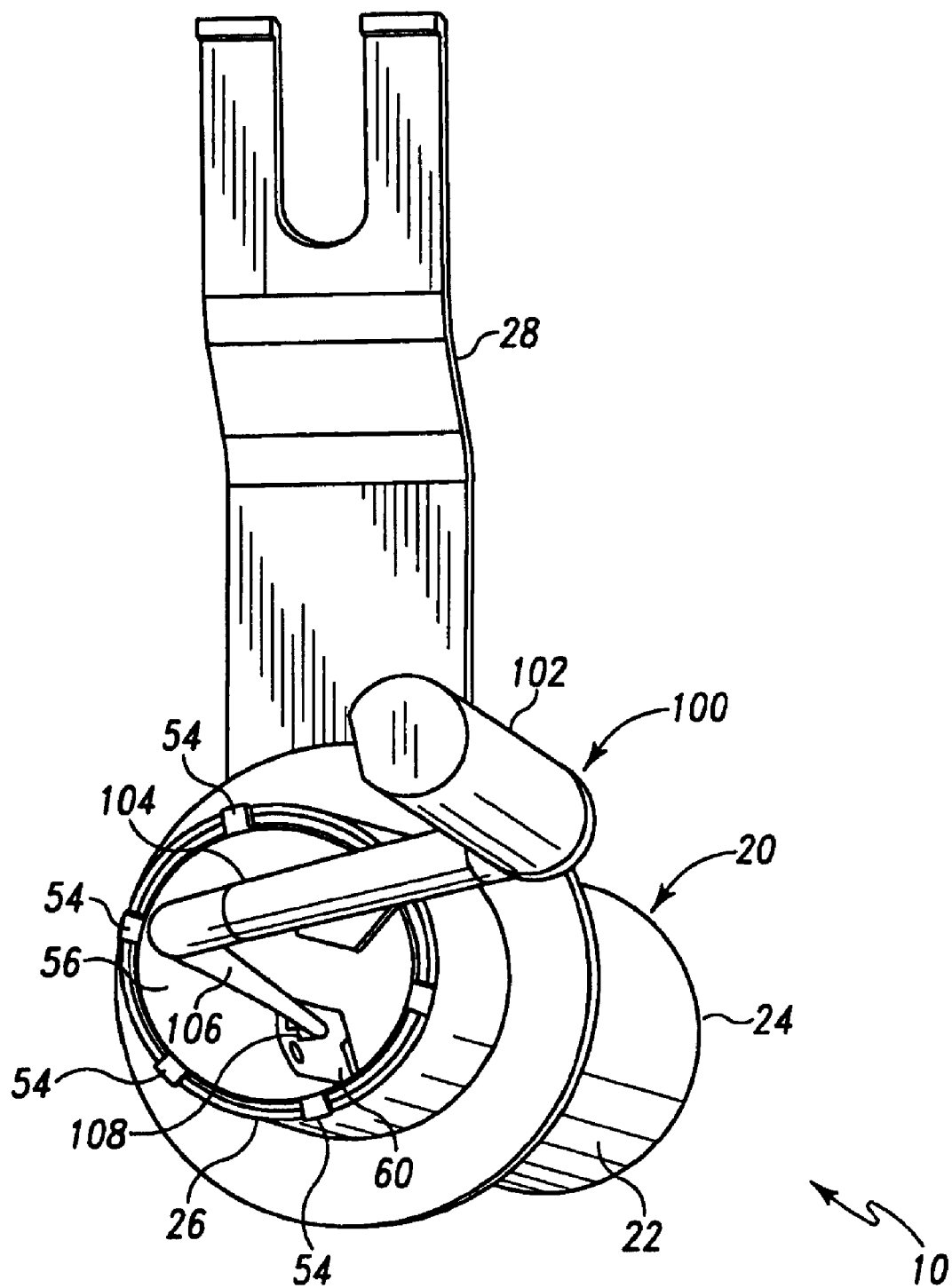
FIG. 4 is a perspective view looking toward the retraction instrument of FIG. 1 with a blade manipulating instrument positioned in the retractor sleeve in contact with a retractor blade.

In FIG. 4, there is shown a blade manipulating instrument 100 positioned in working channel 56. Tool 100 includes a proximal end handle 102, an offset shaft portion 104, and a longitudinal shaft portion 106. A distal engaging member at the end of shaft portion 106 can be engaged in hole 66 of blade 60. Instrument 100 can then be moved to manipulate blade 60 in passage 70 to move it distally or proximally. In one procedure, blade 60 can be advanced distally as shown in FIG. 2 so that it extends distally beyond distal end 24 of retractor sleeve 20. Blade 60 can be extended to provide tissue retraction or a shield along working space WS distally of distal end 24. One or more other blades in the other passages 70 can similarly be selectively extended and retracted in its corresponding passage 70 to provided tissue retraction or shielding.

In one embodiment, tool 100 is a bayoneted hook probe. Other embodiments contemplate other instrument types that can be employed as tool 100. Tool 100 can be engaged to hole 66 as shown. It is also contemplated that the tool can contact the proximal end or any other location along the blade to manipulate the blade.

Figure 5:
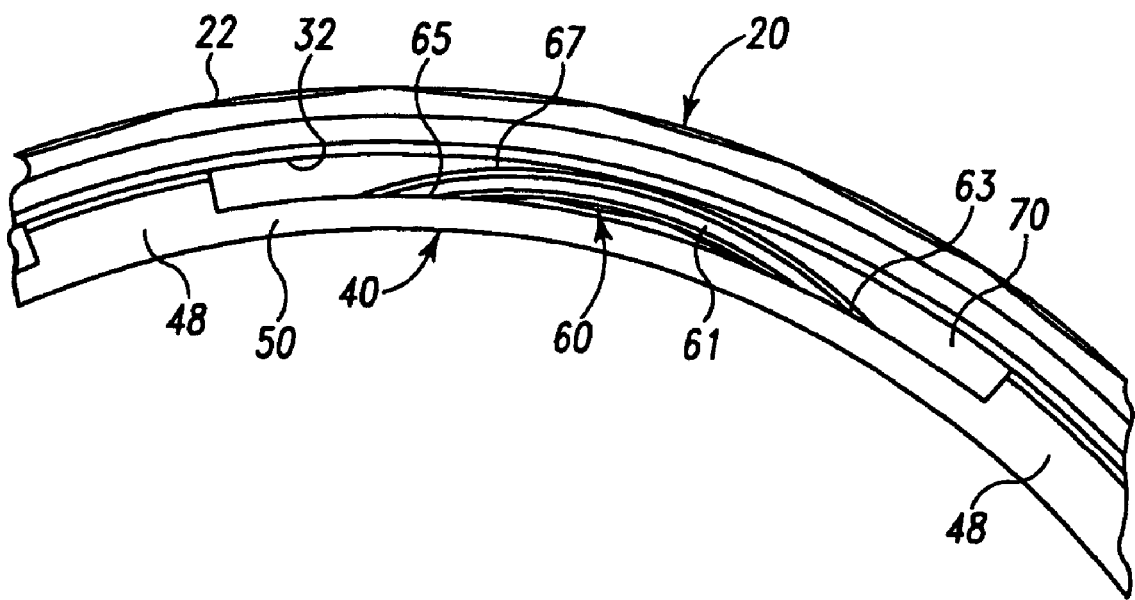
FIG. 5 is an enlarged view of a portion of the retraction instrument of FIG. 1 showing the positioning of a retractor blade between the retaining member and the retractor sleeve.

To maintain blade 60 in passage 70, blade 60 includes a configuration that allows it to frictionally engage an inner surface 32 of retractor sleeve 20 and retaining member 40, as shown in FIG. 5. In FIG. 5, blade 60 extends along an arc 61 between opposite sides 63, 65. Sides 63, 65 contact wall portion 50, while an outer, convexly curved surface 67 of blade 60 contacts inner surface 32 of retractor sleeve 20. The radius of curvature of blade 60 can be sized so that ends 61, 63 are flexed away from one another when outer surface 67 contacts inner surface 32, forcing blade 60 into frictional engagement with retractor 20 and retaining member 40 in passage 70. Accordingly, the curvature of blade 60 along axis 61 is greater than the curvature of wall portion 50 and inner surface 32.

In one embodiment, the distal end of blade 60 can be provided with a curvature that allows the distal end to parallel wall portion 50 and inner surface 32. This allows the distal end of blade 60 to be inserted without frictional engagement with wall portion 50 and inner surface 32. The curvature then transitions at a location proximal of the distal end to the curvature discussed above that allows frictional engagement of the retractor blade 60 with the retractor sleeve 20 and retaining member 40 in a corresponding passage 70.

Other means to maintain blades 60 in the respective passages 70 are also contemplated. For example, the sides 61, 63 can frictionally engage the adjacent flange 48. Interdigitating surfaces can be provided between the blade and one or more of the wall portion 50, inner surface 32, and flanges 48. In another example, a resilient engaging member can be provided along the blades and flanges to resiliently engage the blade while allowing the blade to be moved distally and proximally in passage 70 while retaining the blade in a selected position relative to retractor sleeve 20.

Referring now to FIGS. 6-9, there is shown another embodiment retraction instrument 110 that includes retractor sleeve 20 with another embodiment retaining member 140 and blade 160. Retaining member 140 includes an elongate body 142 extending between a distal end 144 and a proximal end 146. Elongate body 142 includes a semi-cylindrical shape defining an elongate working channel 156 extending therethough between distal end 144 and proximal end 146. Body 142 further includes a number of spaced apart longitudinally extending and radially outwardly projecting intermediate flanges 148 extending between distal and proximal ends 144, 146. Body 142 also includes end flanges 155 extending along and adjacent to longitudinal ends 157.

Wall portions 150 are included between adjacent ones of the flanges 148, 155, and each of the wall portions 150 defines an elongated window 152 in communication with working channel 156. In the illustrated embodiment, windows 152 are centered longitudinally along body 142, although any location along body 142 is contemplated. Longitudinal ends 157 define a gap therebetween such that body 142 is not continuous about working channel 156.

Figure 6:
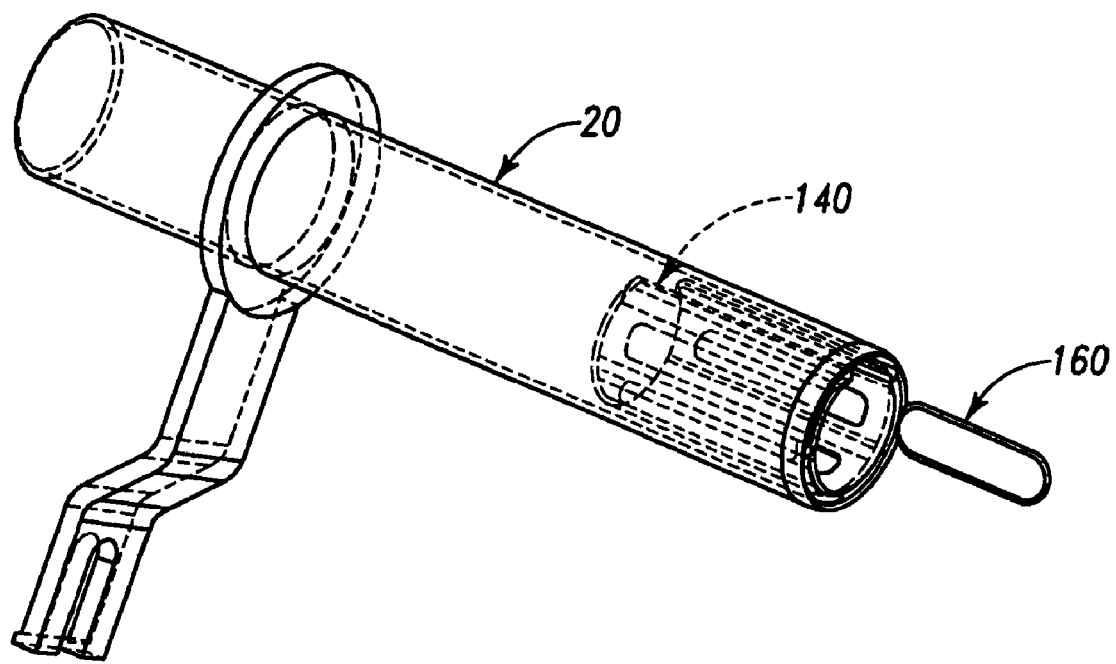
FIG. 6 is a perspective view of another embodiment retraction instrument with the retaining member in the retractor sleeve and a retractor blade withdrawn distally of the retractor sleeve.
Figure 7:
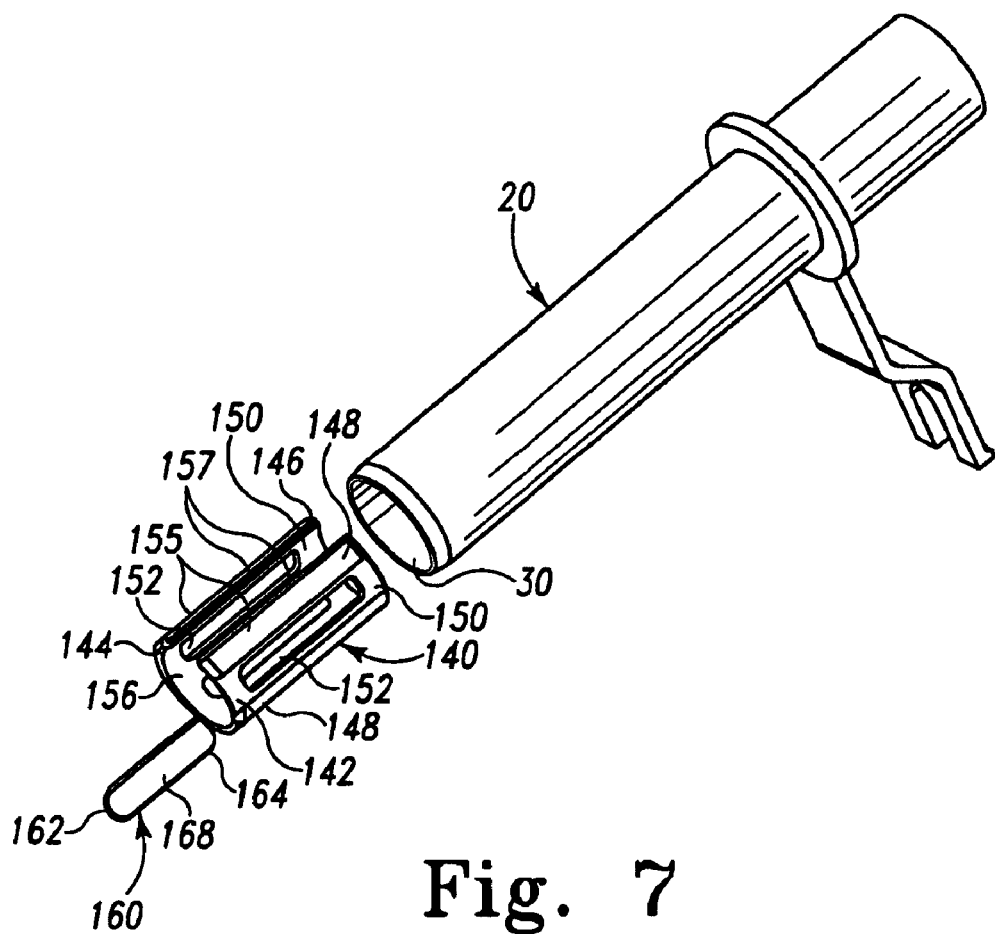
FIG. 7 is an exploded perspective view of the retraction instrument of FIG. 6.
Figure 9:
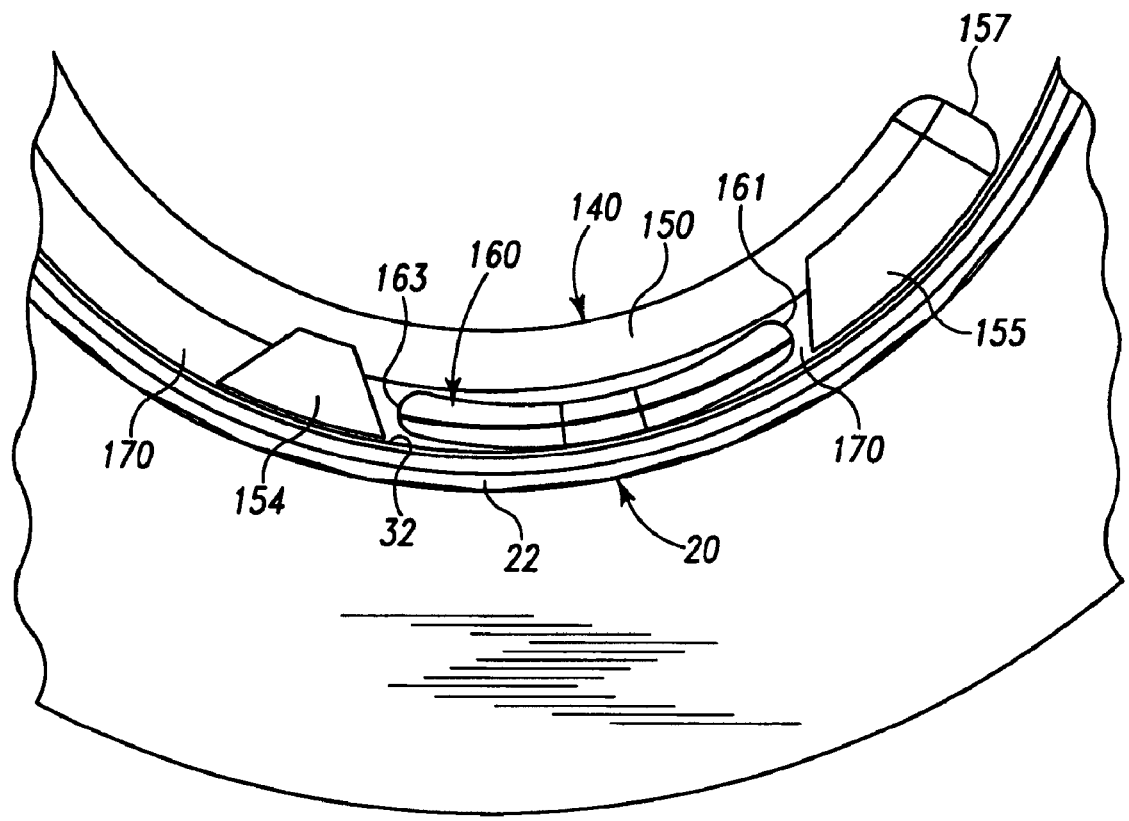
FIG. 9 is an enlarged view of a portion of the retraction instrument of FIG. 6 showing the positioning of a retractor blade between the retaining member and the retractor sleeve.

Retaining member 140 is shown positioned in retractor channel 30 of retractor sleeve 20 in FIG. 6. Ends 157 can be moved toward one another to reduce the gap and radially inwardly flex body 142 to facilitate its insertion into retractor sleeve 20. To maintain retaining member 140 in position in retractor sleeve 20, ends 157 can be released to radially outwardly expand body 142 and spring bias flanges 148, 155 into contact with inner wall surface 32, as shown in FIG. 9. Retaining member 140 can be moved along retractor sleeve 20 until distal end 144 is positioned at or adjacent distal end 24 of retractor sleeve 20.

A passage 170 is formed between an inner wall surface of retractor sleeve 20 and each of the wall portions 150. The passages 170 extend between adjacent ones the longitudinal flanges 148, 155. Working channel 156 is concentric with retractor channel 30, and retractor channel 30 forms an extension of working channel 156 and extends the working channel of the retraction instrumentation 110 to the proximal end of retractor sleeve 20. In one embodiment, the length of body 142 between its distal and proximal ends is less than half of the length between the distal and proximal ends of retractor sleeve 20. Other embodiments contemplate other lengths for retaining member 140.

A blade 160 is shown with an elongated, plate-like body 168 extending between a distal end 162 and a proximal end 164. Blade 160 is positionable into a respective one of the passages 170, and includes a length between distal and proximal ends 162, 164 so that blade 160 can be wholly contained between distal ends 24, 144 and proximal ends 26, 146 of the retractor sleeve 20 and retaining member 140, as shown in FIG. 6. A blade manipulating instrument, such as instrument 100 discussed above, can be inserted in working channel 156. Instrument 100 can then be moved to manipulate blade 160 in passage 170 to move it distally or proximally so that it extends distally beyond distal end 24 of retractor sleeve 20. Blade 160 can be extended to provide tissue retraction or a shield along a working space distally of distal end 24 of retractor sleeve 20. One or more other blades in the other passages 170 can similarly be selectively extended and retracted in its corresponding passage 170 to provided tissue retraction or shielding.

Figure 8:
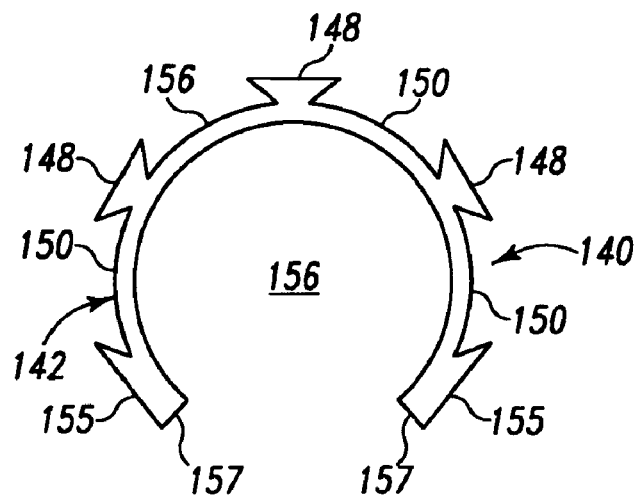
FIG. 8 is a top plan view of a retaining member embodiment employed with the retraction instrument of FIG. 6.

To maintain blade 160 in passage 170, blade 160 includes a configuration that allows it to frictionally engage inner wall 32 of retractor sleeve 20 and retaining member 140 in a manner similar to that discussed above for blade 60 of instrument 10. Other means to maintain blades 160 in the respective passages 170 are also contemplated. For example, the sides 161, 163 can frictionally engage adjacent ones of the flanges 148, 155. In one embodiment, the flanges 148, 155 can include a tapered sidewall configuration as shown in FIG. 8. The taper extends from an outer end surface of the flanges 148, 155 to an inner end of the flanges 148, 155 adjacent the respective wall portion 150. The tapered sidewalls provide a dovetail configuration that can retain the respective blade along wall portion 150. In a further embodiment, interdigitating surfaces can be provided between the blade and either or both of the wall portion 150 and inner surface 32. In another example, a resilient engaging member can be provided on one of the blade or the retaining member to resiliently engage the blade in the passage while allowing the blade to be moved distally and proximally in passage 170.

In another embodiment, there is provided a retaining member that is over-molded about the proximal ends of blades 160. The overmolding maintains the blades in position in passages 170. When and if it is desired to employ the blades to selectively retract distally of the retractor sleeve, the surgeon can remove or sever the over-molding with a scalpel or other cutting instrument to allow one or more of the blades 160 to be slidably moved in passages 170 for tissue retractor distally of retractor sleeve 20. Other removable retaining means for maintaining a positioning of the retractor blades relative to the retaining member are also contemplated.

The gap between longitudinal ends 157 facilitates placement of an endoscope, light, and/or other instrument along working channel 156 without substantially protruding into working channel 156. Furthermore, retaining member 140 can be rotated about inner surface 32 to provide the desired alignment of the endoscope or instrument in the gap, while the body of retaining member 140 can be flexed radially outwardly to frictionally engage an inner surface of the retractor sleeve. In addition, other instruments can be frictionally engaged about the inner surface 32 of retractor sleeve 20 or an inner surface of retaining member body 142 in a manner similar to that in which retaining member 140 is engaged. Such instruments can include, for example, a fiber optic lighting instrument having a C-shaped plate-like body that flexes radially outwardly to engage the inner surface of retractor sleeve 20 or either of the retaining members 40, 140.

In one specific embodiment, the retractor sleeve 20 and blades 60, 160 are each made from surgical grade stainless steel. Other materials are also contemplated, including, for example, plastics and metals and metal alloys, such as spring steel, shape memory metals and alloys, and aluminum. In one embodiment, the blades and retaining member are made from plastic or other inexpensive material and can be disposable after use in a procedure. The retractor sleeve can be autoclavable for re-use. The retractor sleeve can also be made from plastic or other suitable disposable material for disposal with the retractor blades and retaining member. In still a further form, the entire retraction instrumentation can be autoclavable for multiple uses.

Various configurations for working channel 30 are contemplated. Working channel 30 can have a cylindrical shape with, for example, a circular, oval, elliptical, irregular, rounded, or polygonal cross-sectional shape orthogonally to its longitudinal axis. In the lengthwise direction of retractor sleeve 20, working channel 30 can have a uniform size along its length, a proximally tapered frusto-conical shape, a distally tapered frusto-conical shape, an expandable configuration that allows enlargement of the channel of the retractor sleeve, or any other shape or configuration.

In one specific application for spinal surgery, it is contemplated that the blades and retaining member can be loaded into the retractor sleeve after the retractor sleeve is inserted into the incision. Such a procedure can be employed with retaining member 40 and blades 60, for example. In another procedure, retaining member 140 and blades 160 can be inserted into retractor sleeve 20 before retractor sleeve 20 is inserted into the incision.

In either procedure, an incision can be made in the skin and tissue of the patient adjacent the location of a patient's anatomy to be accessed. For example, in spinal surgery, the incision can be made at a vertebral level at a location that provides access to the disc space between adjacent vertebrae or to one or more vertebrae through a desired approach. Prior to insertion of retractor sleeve 20, the skin and tissue S can be sequentially dilated via guidewires and/or one or more dilators of increasing size to form a pathway P through the skin and tissue S to the surgical site in the patient. In such procedures, retractor sleeve 20 is positioned over the last inserted dilator in the pathway P. The working channel formed through retractor sleeve 20 and/or the retaining members 40, 140 provides access to a working space WS at the distal end of retractor sleeve 20 when the guidewires and dilators, if used, are removed therefrom.

For the entire surgery or for certain procedures, it may be desired by the surgeon to extend the length of working channel 30 to facilitate access working space WS below the distal end of retractor sleeve 20, to facilitate access to working space WS by maintaining neural elements and other tissue out of working space WS, and/or to provide a barrier below the distal end of the retractor sleeve 20 to protect anatomical structures from implants and instruments positioned in working space WS. Accordingly, one or more of the blades 60, 160 can be extended from the distal end of retractor sleeve 20 as deemed appropriate by the surgeon. Additional blades can be extended as deemed necessary or desirable during the procedure. The extended blade or blades can further be readily retracted into the retractor sleeve 20 as desired. The depth of the working space WS into the patient can be increased while minimizing trauma to the tissue and skin distal of pathway P. Furthermore, the working space can be extended to areas in the patient to which retractor sleeve 20 cannot be positioned as a result of limitations imposed by its size and/or shape.

Viewing instruments can be positioned in or adjacent to working channel 30 to facilitate surgeon viewing of working space WS and the operative site. For example, an endoscopic viewing element can be mounted on the proximal end of retractor sleeve 20 such that its scope portion extends along channel 30. A microscopic viewing element could be positioned over the proximal end of retractor sleeve 20 for viewing working space WS and the surgical site. Other imaging techniques, such as fluoroscopy, loupes, naked eye, CT scan, and radiographic imaging, for example, can be used alone or in combination with the endoscopic and microscopic viewing elements.

It is further contemplated that other instruments can be mounted on the proximal end of retractor sleeve 20, such as nerve root retractors, tissue retractors, irrigation and/or aspiration instruments, illumination instruments and the like for use in surgical procedures through retractor sleeve 20 in the working space. Surgical instruments and implants can be positioned in or through the working channel 30 to perform surgical procedures or secure the implants in or adjacent the working space WS. The retractor sleeve can be manipulated in the tissue to reposition its distal working end and provide greater access to and increase the size of the working space WS at its distal end.

It is contemplated that for spinal surgery various retractor sleeves 20 can be provided in a kit with various increments of lengths and diameters. The appropriate length and diameter for retractor sleeve 20 will depend on the depth of the desired surgical location below the skin S of the patient, the anatomical location of the surgery, and the patient's anatomy. These factors in retractor selection can be evaluated through preoperative planning prior to surgery by x-rays or other known imaging technique, and can be adjusted during the surgical procedure if necessary since retractors of differing lengths and diameters can be made available.

While the invention has been illustrated and described in detail in the drawings and foregoing description, the same is to be considered as illustrative and not restrictive in character. All changes and modifications that come within the spirit of the invention are desired to be protected.

What is claimed is:

1. A method for retracting tissue in a surgical procedure, comprising:
    inserting a retractor sleeve into an incision of a patient;
    positioning a retaining member in a channel of the retractor sleeve, the retaining member defining a working channel extending at least partially along the channel of the retractor sleeve;
    inserting at least two retractor blades into passages between the retaining member and the retractor sleeve;
    advancing one of the at least two retractor blades distally from a distal end of the retractor sleeve;
    positioning a blade manipulating instrument into the working channel and engaging one of the at least two retractor blades with the blade manipulating instrument through a window formed in the retaining member to apply a force to move the retractor blade; and
    positioning at least one surgical instrument through the working channel of the retaining member.

2. The method of claim 1, wherein:
    the retaining member includes a number of longitudinally extending flanges extending from a body of the retaining member that is located in the channel of the sleeve to an inner surface of the retractor sleeve; and
    the passages are formed between adjacent ones of the longitudinally extending flanges, the longitudinally extending flanges frictionally engaging the at least two retractor blades to maintain the at least two retractor blades in the passages.

3. The method of claim 1, wherein inserting the at least two retractor blades includes frictionally engaging the retractor blades along an inner surface of the retractor sleeve.

4. The method of claim 1, further comprising sequentially dilating the tissue before inserting the retractor sleeve into the incision.

5. The method of claim 1, where the retaining member is positioned in the channel of the retractor sleeve before inserting the retractor sleeve into the incision.

6. The method of claim 1, where the retaining member is positioned in the channel of the retractor sleeve after inserting the retractor sleeve into the incision.

7. The method of claim 1, wherein the retaining member includes opposing longitudinal ends extending between distal and proximal ends of the retaining member, the longitudinal ends forming a gap in the retaining member.

8. The method of claim 7, further comprising flexing the retaining member radially inwardly before positioning the retaining member in the channel of the retractor sleeve and after positioning the retaining member in the channel of the retractor sleeve allowing the retaining member to flex radially outwardly to frictionally engage an inner surface of the retractor sleeve to maintain a positioning of the retaining member in the channel of the retractor sleeve.

9. The method of claim 1, wherein the retaining member includes a body and a number of longitudinally extending flanges spaced thereabout, the body of the retaining member extending along an inner surface of the retractor sleeve to define the passages between the retaining member and the retractor sleeve with the flanges extending between the body of the retaining member and the inner surface of the retractor sleeve, the body of the retaining member further defining the working channel extending between a distal end and a proximal end of the body of the retaining member; and moving each of the at least two retractor blades distally and proximally from a respective one of the passages relative to the distal end of said retractor sleeve.

10. The method of claim 1, wherein the window extends through the retaining member and opens at the working channel and the passages.

11. The method of claim 1, wherein the retaining member includes a body and a number of longitudinally extending flanges spaced thereabout, the body of the retaining member extending along the inner surface of the retractor sleeve to define the passages between the retaining member and the retractor sleeve with the flanges extending between the body of the retaining member and the inner surface of the retractor sleeve, the body of the retaining member further defining the working channel extending between a distal end and a proximal end of the body of the retaining member; and moving each of the at least two retractor blades distally and proximally from a respective one of the passages relative to the distal end of said retractor sleeve.

12. A method for retracting tissue in a surgical procedure, comprising:

inserting a retractor sleeve into an incision of a patient;

flexing a retaining member radially inwardly, the retaining member including opposing longitudinal ends extending between distal and proximal ends of the retaining member, the longitudinal ends forming a gap in the retaining member;

positioning the retaining member in a channel of the retractor sleeve after flexing the retaining member radially inwardly, the retaining member defining a working channel extending at least partially along the channel of the retractor sleeve;

allowing the retaining member to flex radially outwardly to frictionally engage an inner surface of the retractor sleeve to maintain a positioning of the retaining member in the channel of the retractor sleeve;

inserting at least two retractor blades into passages between the retaining member and the retractor sleeve;

advancing one of the at least two retractor blades distally from a distal end of the retractor sleeve; and positioning at least one surgical instrument through the working channel of the retaining member.

13. The method of claim 12, wherein:

the retaining member includes a number of longitudinally extending flanges extending from a body of the retaining member that is located in the channel of the sleeve to the inner surface of the retractor sleeve; and the passages are formed between adjacent ones of the longitudinally extending flanges, the longitudinally extending flanges frictionally engaging the at least two retractor blades to maintain the at least two retractor blades in the passages.

14. The method of claim 12, wherein inserting the at least two retractor blades includes frictionally engaging the retractor blades along the inner surface of the retractor sleeve.

15. The method of claim 12, further comprising sequentially dilating the tissue before inserting the retractor sleeve into the incision.

16. The method of claim 12, wherein advancing one of the at least two retractor blades includes positioning a blade manipulating instrument into the working channel and engaging the one of the at least two retractor blade with the blade manipulating instrument through a window formed in the retaining member to apply a force to move the one of the at least two retractor blades.

17. The method of claim 12, where the retaining member is positioned in the channel of the retractor sleeve before inserting the retractor sleeve into the incision.

18. The method of claim 12, where the retaining member is positioned in the channel of the retractor sleeve after inserting the retractor sleeve into the incision.

19. The method of claim 12, wherein the retaining member includes a number of longitudinally extending windows spaced thereabout and extending through the retaining member and opening at the working channel and the passages.

* * * * *